United States Patent [19]

Andersson

[11] Patent Number: 6,107,333

[45] Date of Patent: *Aug. 22, 2000

[54] PARENTERAL PACLITAXEL IN A STABLE NON-TOXIC FORMULATION

[76] Inventor: Borje S. Andersson, 2632 Carolina Way, Houston, Tex. 77001

[*] Notice: This patent is subject to a terminal disclaimer.

[21] Appl. No.: 09/259,533

[22] Filed: Mar. 1, 1999

Related U.S. Application Data

[63] Continuation of application No. 08/672,594, Jun. 28, 1996, Pat. No. 5,877,205.

[51] Int. Cl.⁷ ............... A61K 31/337; A61P 33/00
[52] U.S. Cl. ............................. 514/449; 549/510
[58] Field of Search ............... 514/449; 549/510

[56] References Cited

U.S. PATENT DOCUMENTS

| | | | |
|---|---|---|---|
| 5,430,057 | 7/1995 | Andersson et al. | 514/517 |
| 5,597,820 | 1/1997 | Hausheer | 514/283 |

OTHER PUBLICATIONS

Andersson et al., "KBM–7, A Human Myeloid Leukemia Cell Line with Double Philadelphia Chromosomes Lacking Normal c–ABL and BCR Transcripts," *Leukemia*, 9:2100–2108, 1995.

Andersson et al., "Nucleotide Excision Repair Genes as Determinants of Cellular Sensitivity to Cyclophosphamide Analogs," *Cancer Chemother Pharmacol*, 38:406–416, 1996.

Andersson et al., "The Role of DNA Damage in the Resistance of Human Chronic Myeloid Leukemia Cells to Cyclophosphamide Analogues," *Cancer Research*, 54:5394–5400, 1994.

Andersson et al., "Ph–Positive Chronic Myeloid Leukemia with Near–Haploid conversion In Vivo and Establishment of a Continuously Growing Cell Line wit Similar Cytogenetic Patter," *Cancer Genet Cytogenet*, 24:335–343, 1987.

Brown et al., "A Phase Trial of Taxol Given by a 6–Hour Intravenous Infusion," *J Clincal Oncology*, 9(7):1261–1267, 1991.

Chevallier et al., "Docetaxel is a Major Cytotoxic Drug for the Treatment of Advanced Breast Cancer: A Phase II Trial of the Clincal Screening Cooperative Group of the European Organization for Research and Treatment of Cancer," *J Clinical Oncology*, 13(2):314–322, 1995.

Eiseman et al., "Plasma Pharmacokinetics and Tissue Distribution of Paclitaxel in $CD_2F_1$ Mice," *Cancer Chemother Pharmacol*, 34:465–471, 1994.

Fornter et al., "Fat Emulsion Vehicle for Intravenous Administration of an Aqueous Insoluble Drug," *Amer J Hospital Pharm*, 32:582–584, 1975.

Gallagher et al., "Characterization of the Continuous, Differentiating Myeloid Cell Line (HL–690) from a Patient with acute Promyelocytic Leukemia," *Blood*, 54(3):713–733, 1979.

Hansen et al., "Re–Examination and Further Development of a Precise and Rapid Dye Method for Measuring Cell Growth/Cell Kill," *J Immunological Methods*, 119:203–210, 1989.

Holmes et al., "Phase II Trial of Taxol, an Active Drug in the Treatment of Metastic Breast Cancer," *J National Cancer Institute*, 83(24):1797–1805, 1991.

Keating et al., "L–Asparaginase and PEG Asparaginase–Past, Present and Future," *Leukemia and Lymphoma*, 10:153–157, 1993.

Kim, "Preclinical Toxicology and Pharmacology of Dimethylacetamide, with Clincal Notes," *Drug Metabolism Reviews*, 19(3&4):345–368, 1988.

Lockard et al., "Efficacy and Toxicity of the Solvent Polyethylene Glycol 400 in Monkey Model," *Epilepsia*, 20:77–84, 1979.

Mann and Whitney, "On a Test of Whether One of Two Random Variables is Stochastically Larger than the Other," *Ann Math Statist*, 18(1):50–60, 1947.

Nicoletti et al., "Antitumor Activity of Taxol (NSC–125973) in Human Ovarian Carcinomas Growing in the Peritoneal Cavity of Nude Mice," *Annals of Oncology*, 4:151–155, 1993.

Parthasarathy et al., "Interaction of Lipsome–Associated All–Trans–Retinoic Acid with Squamous Carcinoma Cells," *Cancer Chemother Pharmacol*, 34:527–534, 1994.

Rizzo et al., "Analysis of Anticancer Drugs in Biological Fluids: Determination of Taxol with Application to Clinical Pharmacolkinetics," *J Pharmaceut Biomed Anal*, 8(2):159–164, 1990.

Rose, "Taxol–Based Combinational Chemotheraphy and Other In Vivo Preclincal Antitumor Studies," *J National Cancer Institute*, 15:47–53, 1993.

Rowinsky et al., "Taxol: A Novel Investigational Antimicrotubule Agent," *J National Cancer Institute*, 82(15):1247–1259, 1990.

Rowinsky et al., "The Current Status of Taxol," In: *Principles and Practice of Gynecolgic Oncology Updates*, Hoskins et al. (Eds.), 1(1):1–16, 1993.

Seidman et al., "Paclitaxel as Second and Subsequent Therapy for Metastatic Breast Cancer: Activity Independent of Prior Anthracycline Response," *J Clinical Oncology*, 13(5):1152–1159, 1995.

(List continued on next page.)

*Primary Examiner*—Evelyn Mei Huang

[57] ABSTRACT

Disclosed is a stable and effective formulation of a taxane analog, preferably paclitaxel. The formulation comprises a dimethylacetamide and polyethylene glycol solution of the drug that is diluted into an aqueous lipid emulsion prior to use. The formulation is effective as a parenterel drug against taxane sensitive tumors.

14 Claims, 12 Drawing Sheets

OTHER PUBLICATIONS

Sharma et al., "Reversed–Phase High–Performance Liquid Chromatographic Determination of Taxol in Mouse Plasma," *J Chromatography B*, 655:315–319, 1994.

Spiegel and Noseworthy, "Use of Nonaqueous Solvents in Parenteral Products," *J Pharm. Sci.*, 52(10):917–927, 1963.

Verweij et al., "Paclitaxel (Taxol™) and docetaxel (Taxotere™): Not Simply Two of a Kind," *Annals of Oncology*, 5:495–505, 1994.

Weiss et al., "A Phase I Study of Dimethylacertamide," *Cancer Chemotheraphy Reports*, 16:477–485, 1962.

Weiss et al., "Hypersensitivity Reactions from Taxol," *J Clincal Onoclolgy*, 8(7):1263–1268, 1990.

Willey et al., "High–Performance Liquide Chromatographic Procedure for the Quantative Determination of Paclitaxel (Taxol®) in Human Plasma," *J Chromatography*, 621:231–238, 1993.

Sparreboom et al., "Nonlinear Pharmacokinetics of Paxlitaxel in Mice Results from the Pharmaceutical vehicle Chremophor EL," Cnacer Research, 56:2112–2115, May 1996.

PARENTERAL PACLITAXEL IN A STABLE NON-TOXIC FORMULATION

This is a continuation of application Ser. No. 08/672,594 filed Jun. 28, 1996, which issued as U.S. Pat. No. 5,877,205 on Mar. 2, 1999.

The present invention relates to formulations of taxane analogs that are useful for the treatment and suppression of malignant disease without exposing the patient to the side effects of polyoxyethylated castor oil or ethyl alcohol.

BACKGROUND OF THE INVENTION

Paclitaxel is one of the most promising chemotherapeutic agents that has entered clinical testing in the last decade. It has shown impressive activity against ovarian and mammary carcinomas, and is currently undergoing clinical phase II–III trials against several different malignancies. The available results indicate, that the drug may be of considerable value also against lymphomas and different kinds of leukemia. The supply of the drug has been limited due to cumbersome extraction methodology, that as its exclusive starting material utilized the bark of the pacific yew tree. This shortcoming has to some extent been alleviated by the recent development of techniques to extract paclitaxel from the needles of the yew tree as well as from the bark. Technology has also been developed for the semisynthetic production of taxol from naturally available precursor substances that are in abundant supply. Although paclitaxel is now available for parenteral administration, there is only one formulation that is approved for human use, available from Bristol-Myers-Squibb (Taxol™). This formulation contains 50% (v/v) alcohol, as well as an 88-fold excess of polyoxyethylated castor oil (Cremophor® EL), which has a potential for inducing serious side effects. The acute and common clinical side effects of the available paclitaxel formulation are severe: listing dyspnea, hypotension, angioedema, generalized urticaria, and most notably anaphylactoid reactions, with risk for a fatal outcome. In addition, the high Cremophor® EL concentrations facilitate the leaking of "plasticizers", i.e., chemicals used in the manufacture of disposable infusion bags and iv tubing sets into the infusate, and the (long-term) risks of patient exposure to these chemicals is unknown. This experience of severe acute side effects from the currently used drug preparation has mandated premedication with diphenhydramine, $H_2$-antagonists, and even corticosteroids.

There is need, therefore, for formulations of taxanes based on alternative solvent systems. This would alleviate dangerous side effects and provide a more even drug supply for both conventional dose therapy and for high dose chemotherapy using paclitaxel and related taxane compounds.

SUMMARY OF THE INVENTION

The present invention seeks to overcome these drawbacks in the prior art by providing a reformulated drug using non-toxic solvent systems based on the principle of cosolvency to provide alternative, pharmaceutically acceptable solvent vehicles that yield stable drug formulations while eliminating the use of Cremophor® EL and ethyl alcohol. These formulations potentially modulate the drug's pharmacokinetics/pharmacodynamics after intravascular administration and possibly also alter the side effect spectrum, since e.g., the currently used paclitaxel regimens mandate the administration of as much as 20–30 ml of Cremophor® EL in the average size adult patient.

The invention may also be described in broad aspects as the discovery of compositions and procedures for solubilizing taxane analogs for parenteral use, utilizing paclitaxel as the prototype substance. As an example of the present discovery, a taxane analog such as paclitaxel is dissolved in an organic solvent as the primary vehicle, i.e., dimethylacetamide (DMA) or dimethylsulfoxide (DMSO), and then followed with a secondary solvent, such as polyethyleneglycol 400 (PEG), to stabilize the drug in solution for subsequent (final) dilution in an aqueous solvent. A preferred final solvent is an aqueous lipid emulsion such as e.g., emulsified soy bean oil (Intralipid™, from Kabi-Pharmacia Inc., Stockholm, Sweden). Although the examples described herein utilize polyethylene glycol having an average molecular weight of about 400, it is understood that the molecular weight of the PEG may vary, from about 300 to about 10,000. In addition, other co-solvents that are contemplated to be effective include but are not limited to solvents such as e.g., various amides examples of which are 2-pyrrolidinone, 1-methyl-2-pyrrolidinone, and further sulfur containing compounds such as sulfolane, tetramethylenesulfon and tetramethylenesulfoxide. These agents are all examples of dipolar aprotic solvents which should be possible to use for the solubilization of taxane compounds, although they have little or no previous established recorded use as pharmaceutical solvents.

The preferred lipid solvent offers certain advantages because paclitaxel, as a prototype taxane analog, is highly lipophilic and the use of an aqueous lipid emulsion is contemplated to stabilize the agent in the aqueous diluent, such that the therapeutic value of infusions in excess of 24 hours can be systematically and conveniently investigated without loss of drug activity due to precipitation or degradation. Intralipid is readily available and is approved for routine parenteral nutritional support. It is understood that other lipid emulsions that are known in the art to be non toxic and hypoallergenic in man. Analogously usable lipid emulsions include Liposyn®, Soyacal®, and Travemulsion®.

Furthermore, paclitaxel is light sensitive and the use of an aqueous lipid emulsion as the final solvent will provide protection against light while the drug is infused.

One paclitaxel formulation according to the present invention is demonstrated to be stable at 25 mg/ml for several months at room temperature. The final use formulation is stable at 1–5 mg/ml for at least 7 days, and retains full cytoxic activity when assayed against two human leukemic cell lines using the commercially available formulation as the reference solution. Further, the vehicle formulation itself is non-toxic as assayed in a hemolysis assay. Another formulation has been used to demonstrate that clearly cytocidal concentrations of paclitaxel are maintained for many hours in a rodent model after injection of 3 mg/kg body weight. Therefore, the formulations described herein provide pharmaceutically acceptable alternatives to the currently available paclitaxel preparation for intravascular infusion therapy of malignant disease in man and domestic animals, with the potential benefit of having considerably less side effects than the currently available clinical preparation. Malignant diseases treatable with the preparations of the present invention include human ovarian cancer, breast cancer, malignant lymphoma, lung cancer or Kaposi's sarcoma. It should be possible to extrapolate the use of these novel solvent systems for solubilization of other (lipophilic) taxane analogs to facilitate clinical studies of these very active anticancer agents.

Advantages of the present invention include:

1. pharmaceutically stable and parenterally acceptable novel formulations of lipophilic taxane analogs, that can be utilized for the treatment of malignant disease in man and domestic animals. The resulting formulations are based on the pharmaceutical principle of cosolvency, which is commonly utilized in the pharmaceutical industry, and approved by the FDA;

2. new formulations that can be mixed with clinically acceptable, aqueous parenteral infusion fluids as final solvent(s);

3. new formulations that retain full cytotoxic activity as assessed in tissue cultures, utilizing human malignant cell lines as targets; and 4. formulations that are acceptable for intravascular administration, with pharmacokinetics comparable to those obtained with the previously available formulation after intravenous administration of this formulation in a rat model.

The present invention provides compositions and methods for the solubilization of taxane analogs (e.g., paclitaxel) in complex, pharmaceutically acceptable liquid vehicles that avoid the use of polyoxyethylated castor oils such as Cremophor® or ethyl alcohol, such that the drugs remain physically and chemically stable and can be administered intravascularly without undue toxicity from undissolved drug and/or from the solvent vehicle at drug doses contemplated to be effective to exhibit clinically significant tumoricidal effects.

According to the principle of cosolvency, preferred formulations utilize combinations of anhydrous N,N-dimethylacetamide (DMA), dimethylsulfoxide (DMSO), and polyethylene glycol-400 (PEG) as the primary (stock) solvents that are miscible in secondary/final aqueous solvents, examples of which are normal saline, 5% dextrose in water and, lastly, an aqueous soy bean lipid emulsion (Intralipid™). These solvents are examples of vehicles in which taxane analogs, such as paclitaxel, are suitably solubilized and safe for human administration, alone or in combinations with other drugs.

The described vehicles may be utilized to dissolve paclitaxel in concentrations ranging from 0.1 to more than 25 mg/ml. This range is contemplated to cover the administration of dosages necessary to yield active cytotoxic concentrations in vivo to treat malignancies sensitive to these drugs. The invention will therefore allow the introduction of paclitaxel and other taxane analogs in clinical practice for the therapy of malignant disease without exposing the patient to the serious and potentially deleterious effects of Cremophor® EL, ethyl alcohol or other undesirable solvents.

In a broader sense, the present invention describes a method to administer poorly water-soluble taxane analogs such as paclitaxel intravascularly. This embodiment circumvents the poor intestinal absorption of the drug as well as avoids the serious systemic adverse effects of polyoxyethylated castor oil and ethyl alcohol that have been encountered with the only currently available formulation of this agent. The remarkable stability of the new formulations will allow prolonged parenteral infusion in contrast to the presently available formulation's lack of extended stability in clinically acceptable infusion fluids, and is thus contemplated to enhance the therapeutic potential of these drugs.

ABBREVIATIONS USED IN THIS APPLICATION

ATCC; American Tissue Culture Collection, Rockville, Md.

Cremophor® EL; Brand name for polyoxyethylated castor oil

DMA; anhydrous N,N-dimethylacetamide

DMF; Dimethylformamide

FDA; Federal Food and Drug Administration

HPLC; High pressure liquid chromatography

HL-60; Human myeloid leukemia cell line

IMDM; Iscove's modified Dulbecco Medium (GIBCO, Grand Island, New York, N.Y.)

Intralipid™; Brand name of an aqueous lipid emulsion, made from soy bean oil, and marketed for parenteral nutrition by Kabi-Pharmacia, Inc., Stockholm, Sweden KBM-7/B5; Human myeloid leukemia cell line MeOH: Methanol MTT; 3,[4,5-dimethylthiazol-2-yl]2,5-diphenyltetrazolium-bromide NCI; National Cancer Institute $NH_4$-acetate; Ammonium acetate NS; Normal saline (150 mM NaCl)

PBS; Phosphate buffered saline (Dulbecco's formulation, pH 7.4)

PEG; Polyethylene glycol-400

PG; Propylene glycol

PTFE; Polytetrafluorethylene (filters), Teflon™

RT; Room temperature (22° C.)

Sep Pak Vac1 cc tC2™; disposable extraction columns from Waters Inc., Milford, Mass.

SDS; Sodium dodecylsulphate

DESCRIPTION OF ILLUSTRATIVE EMBODIMENTS

Figure 1:
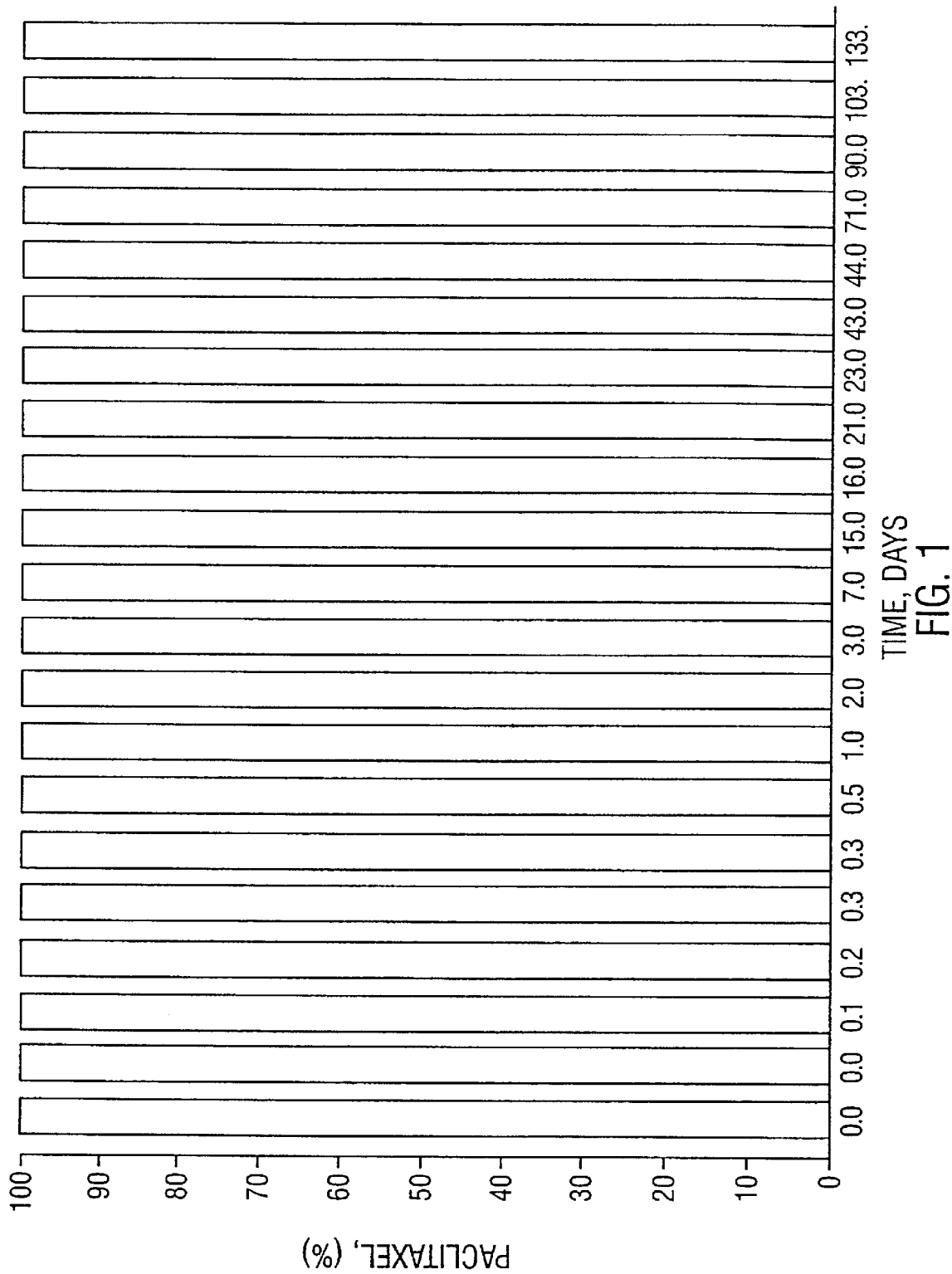
FIG. 1. Stability of paclitaxel at room temperature (RT, 22° C.) and at 4° C. in the DMA:PEG (1:3, v/v) stock formulation at a concentration of 25 mg/ml. The stability at 4° C. is to date (4.5 months) overlapping with that recorded for the samples stored at RT.

The present invention provides formulations for the parenteral or intravascular administration of poorly water soluble taxane analogs, which lack both alcohol and polyoxyethylated castor oil and are useful to improve the control of malignancies that are sensitive to these agents. Exemplary formulations are shown herein to be effective when applied to art accepted models for human malignancies, e.g. the human leukemic cell lines KBM-7/B5 and HL-60. This use of taxanes such as paclitaxel and docetaxel, that is, as parenteral anticancer agents, has been previously demonstrated in the practice of medicine, and they have well documented cytotoxic properties in vitro as well as in the clinical setting (Rowinsky et al., 1990; Nicoletti et al., 1993; Rose, 1993; Verweij et al., 1994; Rowinsky et al., 1993; Brown et al., 1991; Holmes et al., 1991; Seidman et al., 1995; Chevallier et al., 1994).

Parenteral administration is the preferred approach for taxane analogs as therapy for systemic malignancies. Unfortunately, most of these drugs have an exceedingly low solubility in most physiologically acceptable aqueous solvents that would be compatible with intravascular administration. The solvent system for the commercially available paclitaxel formulation is based on a combination of ethyl alcohol and polyoxyethylated castor oil, which brings a potential for serious side effects. Paclitaxel in this "standard" vehicle has proven to have acute side effects of a primarily anaphylactoid nature, necessitating extensive premedication with diphenhydramine, histamine $H_2$ antagonists and even corticosteroids (Weiss et al., 1990; TAXOL® (Paclitaxel)). The formulations disclosed herein, which are based on the principle of cosolvency (Spiegel and Noseworthy, 1963; Yalkowsky and Roseman, 1981) demonstrate the ability to solubilize taxane analogs like paclitaxel without affecting their cytotoxic properties.

The preferred solvents are virtually nontoxic and proven safe for administration in experimental animals and humans in the proposed concentrations and total doses to be utilized. Indeed, DMA has previously been used for solubilization of various pharmacologically active agents administered in man (U.S. Department of Health and Human Services, 1984; Weiss et al., 1962; Kim, 1988). The parenteral administration of PEG has been studied in detail in a simian model (Lockard et al., 1979), and PEG has also been used clinically as a (covalently bound) carrier of L-Asparaginase in the treatment of lymphocytic leukemia and lymphoma (Keating et al., 1993). DMSO has been extensively used in clinical medicine, most widely utilized as a cryoprotective agent for cryopreservation of bone marrow and peripheral blood progenitor cells prior to high dose chemotherapy and hemopoietic stem cell transplantation (Davis and Rowley, 1990; Gorin, 1992). No serious clinical adverse effects have been experienced from the use of these diluents. The clinical use of normal saline (NS), dextrose in water (5–70%), and the aqueous lipid emulsion are well established routine means to correct fluid and electrolyte balance and to supply parenteral nutrition. Normal saline and dextrose in water are extensively used to dilute various medications for parenteral use. Although the aqueous lipid emulsion has not yet found wide spread use as a pharmaceutical diluent, this use has been suggested (Fortner et al., 1975). The data obtained in the rodent model demonstrate that the proposed stable taxane formulation will allow parenteral treatment of systemic malignancies and will provide 100% bioavailability of the drug without exposing the patient to ethyl alcohol and Cremophor® EL. After a brief iv infusion of paclitaxel, the plasma concentrations clearly reach, and for extended time, remain in the antineoplastic range as established by in vitro studies of cytotoxic activity against human malignant cell lines. Specifically, the paclitaxel use-formulation disclosed herein is chemically stable for more than one week at RT, is simple to handle and provides reliable and easily controlled dosing with 100% bioavailability of the drug.

In summary, the present discovery provides improvements in the methods and formulations used in the treatment of certain malignancies, such as ovarian cancer, breast cancer and Kaposi's sarcoma in immunocompromised patients, by allowing the administration of paclitaxel for prolonged time periods. These methods and formulations provide the further advantage of eliminating the risk of side effects associated with the use of alcohol and/or polyoxylated castor oil in the preparation of lipophilic agents.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Taxane Analog Formulations Acceptable for Parenteral Administration

Calculation of the Desired Solubility

A relevant solubility range for paclitaxel has been calculated by extrapolation from doses known to have significant antitumor efficacy in man. These studies have all been conducted using the ethyl alcohol/Cremophor® EL preparation, which presently is the only FDA-approved parenteral formulation. The currently utilized paclitaxel regimens typically prescribe a dose in the range of 135–250 $mg/m^2$ of body surface (Verweij et al., 1994; Rowinsky et al., 1993; Brown et al., 1991; Holmes et al., 1991; Seidman et al., 1995; TAXOL® (Paclitaxel)). The clinically most efficient mode of administration of paclitaxel is not yet known. It is apparent however, that with a prolonged infusion mode the neurologic side effects of the drug are less pronounced than that experienced with short (3 hours) infusions. It is therefore assumed, that the clinically most optimal administration mode for paclitaxel is a prolonged infusion, possibly over more than 24 hours, necessitating a use-formulation with a desired stability at RT of at least 36–48 hours to allow for convenient handling. If such a dose were dissolved at a concentration of 1–5 mg/ml, a stock formulation of at least 10–25 mg/ml would be preferable to allow for suitable handling with dilution to a fairly wide range of use-concentrations that can be easily infused over the required prolonged time interval without the need for repeated exchanges of the infusion fluid due to physical or chemical degradation of the drug in the infusate.

Enhanced Solubility in Physiologically Acceptable Solvents

The solubility of paclitaxel was determined in several individual vehicles. A known amount of the drug, as a powder (two different aliquots of purified drug were obtained from Xechem Inc. New Brunswick, N.J.), was equilibrated in the respective solvent at RT (22° C.) over 1 hour. An aliquot was then removed and diluted in MeOH prior to HPLC at predetermined times. Based on the paclitaxel solubility in these particular vehicles, it was then attempted to enhance the (stable) solubility by mixing different solvents according to the cosolvency principle (Spiegel and Noseworthy, 1963; Yalkowsky and Roseman, 1981). Different solvent systems were evaluated relative to the above estimates of necessary solubility to arrive at a clinically relevant stable stock formulation. This stock formulation would then be diluted with a "final solvent" to yield a complete stable clinical working formulation of 1–5 mg/ml, that could be infused parenterally. The final solvent was selected from one of the commonly utilized parental infusion fluids, NS, 5% dextrose in water or a parenterally acceptable aqueous lipid emulsion (e.g., Intralipid), all of which are readily available and approved for parenteral administration.

HPLC Assay

A most accurate and sensitive detection system for low concentrations of paclitaxel in solution, both protein-containing and protein-free mixtures, would be an HPLC assay utilizing absorbance detection with a detector operating in the uv spectrum at 227 nm, a value chosen on the basis of the inherent absorption maxima of the paclitaxel molecule. This general approach has previously been described by several investigators (Rizzo et al., 1990; Willey et al, 1993; Sharma et al., 1994; Eiseman et al., 1994).

A liquid chromatographic system equipped with an LDC 4000 multi-solvent delivery system™ and a Water system 717plus Autoinjector™ was employed. The absorbance detector was a LDC 3100 variable wave length detector in sequence with an LDC model CI 4100 fully computerized integrator. The column used was initially a Waters $\mu$Bondapak™ phenyl column, 3.9×300 mm, and later a Waters CiSymmetry™ column, 3.9×150 mm (Millipore Corp., Marlborough, Mass.) was used. The isocratic mobile phase system consisted of $NH_4$-acetate (20 mM, pH 5.0)/acetonitrile/MeOH (in volume ratios of 50:40:10). All chemicals were HPLC grade unless otherwise indicated. The flow rate was 1.0 ml/min and the recorder's chart speed was 5 mm/min. The analytic system was established from (Rizzo et al., 1990; Willey et al., 1993; Sharma et al., 1994; Eiseman et al., 1994; Unpublished Method: Courtesy of Xechem Inc., Newark, N.J., and from an unpublished method, courtesy of Dr T. Madden, Department of Pediatrics, UT MD Anderson Cancer Center).

The appearance of endogenous plasma (protein) peaks in the chromatogram caused interference with the HPLC elution in the pharmacologic study. Therefore, an extraction/purification step was added with disposable Sep Pak Vac 1 cc tC2 extraction columns (Waters Corporation Inc., Milford, Mass.). These disposable extraction columns were conditioned with 1 ml of MeOH and 1 ml water with 500 $\mu$l of MeOH:water (85:15, v/v) as the mobile phase. The eluate was then analyzed by HPLC as above.

Paclitaxel Solubility

Several strategies were evaluated to solubilize paclitaxel in water-miscible, physiologically acceptable vehicles that would be compatible with human administration. The examined candidate solvents included DMA, DMSO, PEG, and PG, in addition to the aqueous solvents NS, 5% dextrose in water and an aqueous soy bean lipid emulsion (Intralipid). DMA and DMSO were the best primary solvents, whereas paclitaxel, as expected, was insoluble in most of the aqueous solvents (Table 1). Only with DMA and DMSO was a solubility in excess of 10 mg/ml reached. Actually, both these solvents yielded paclitaxel concentrations in excess of 100 mg/ml and the drug remained stable in solution for over 4 hours at RT. However, although paclitaxel could be dissolved in DMA and DMSO to at least 100 mg/ml, the drug started degrading within about 12 hours in the solvent. Due to a concern that DMSO could possibly be chemically reactive with the taxanes, most studies addressed how to stabilize paclitaxel dissolved in DMA with a cosolvency approach Spiegel and Noseworthy, 1963; Yalkowsky and Roseman, 1981). Several cosolvent combinations were investigated; the addition of PEG allowed for a stable solution of 25 mg/ml (FIG. 1 and FIG. 2), and when this stock solution was further diluted to 1 mg/ml or 5 mg/ml with an aqueous lipid emulsion, the resulting "use-formulation" was stable for at least 7 days at RT (see FIG. 3).

HPLC Assay

Figure 4:
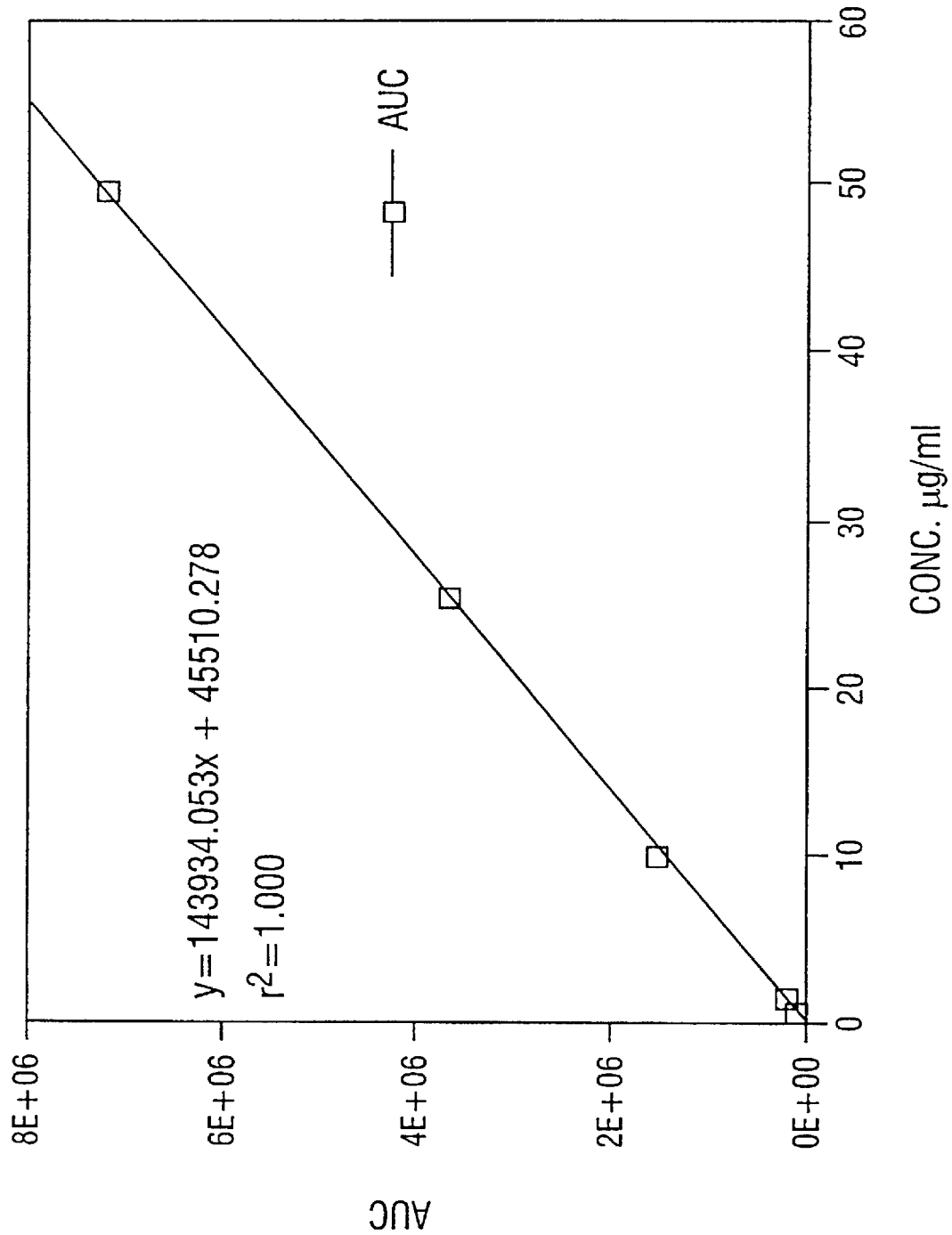
FIG. 4. Standard curve of paclitaxel concentration vs. area under the curve (AUC) for the HPLC assay used in the stability studies. An analogous standard curve was prepared for the pharmacology study.
Figure 5A:
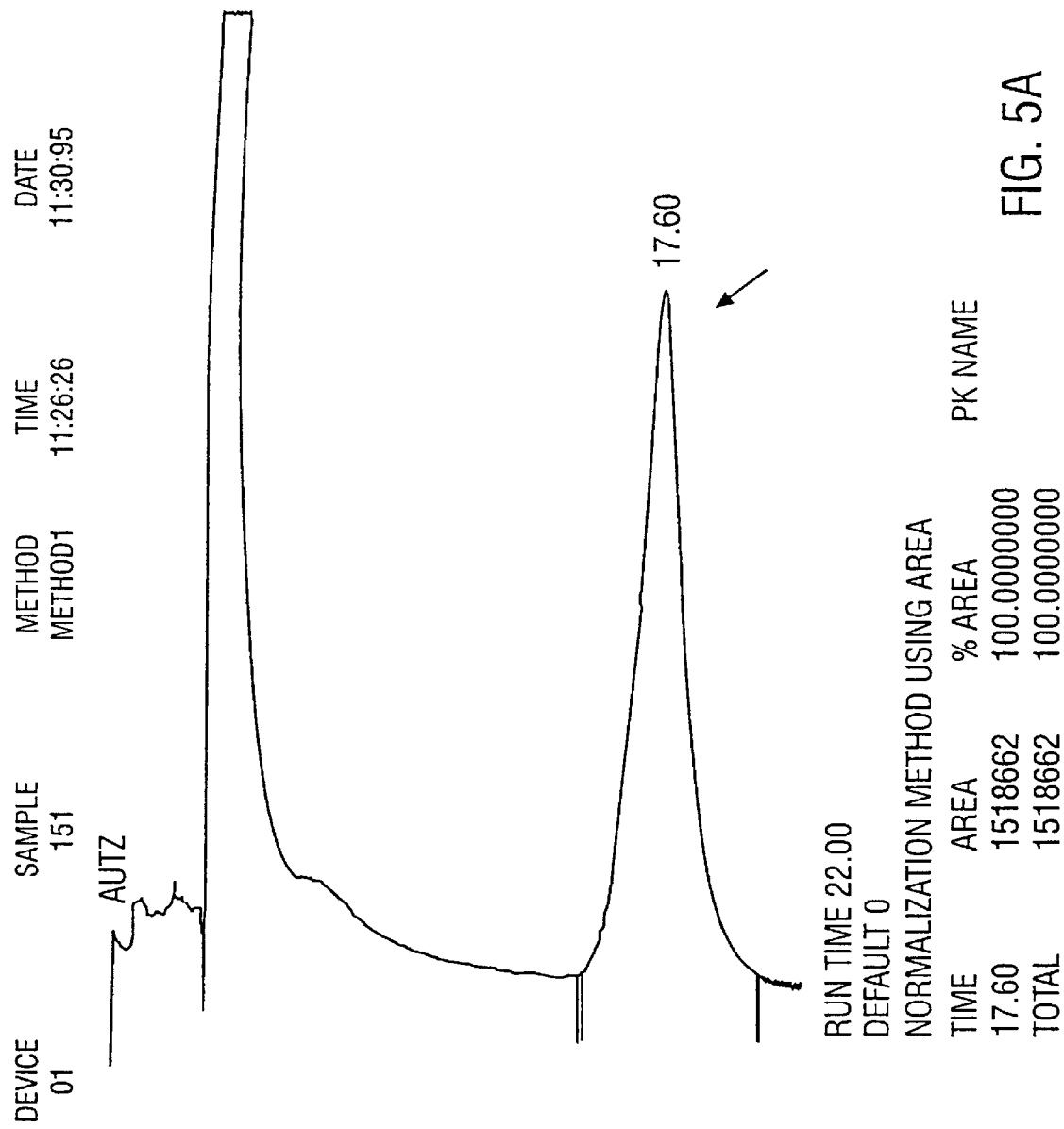
FIG. 5A–FIG. 5B are examples of chromatograms obtained from HPLC assays in the stability studies, in FIG. 5A using the Waters μBondapak Phenyl column. The injected sample volume (10 μg/ml) was 20 μl in FIG. 5B and in FIG. 5C the $C_8$ Symmetry™ column was used, injected volume was 20 μl (FIG. 5B; 1 μg/ml, and in FIG. 5C; 10 μg/ml). The HPLC conditions were as described under Example 1.
Figure 5B:
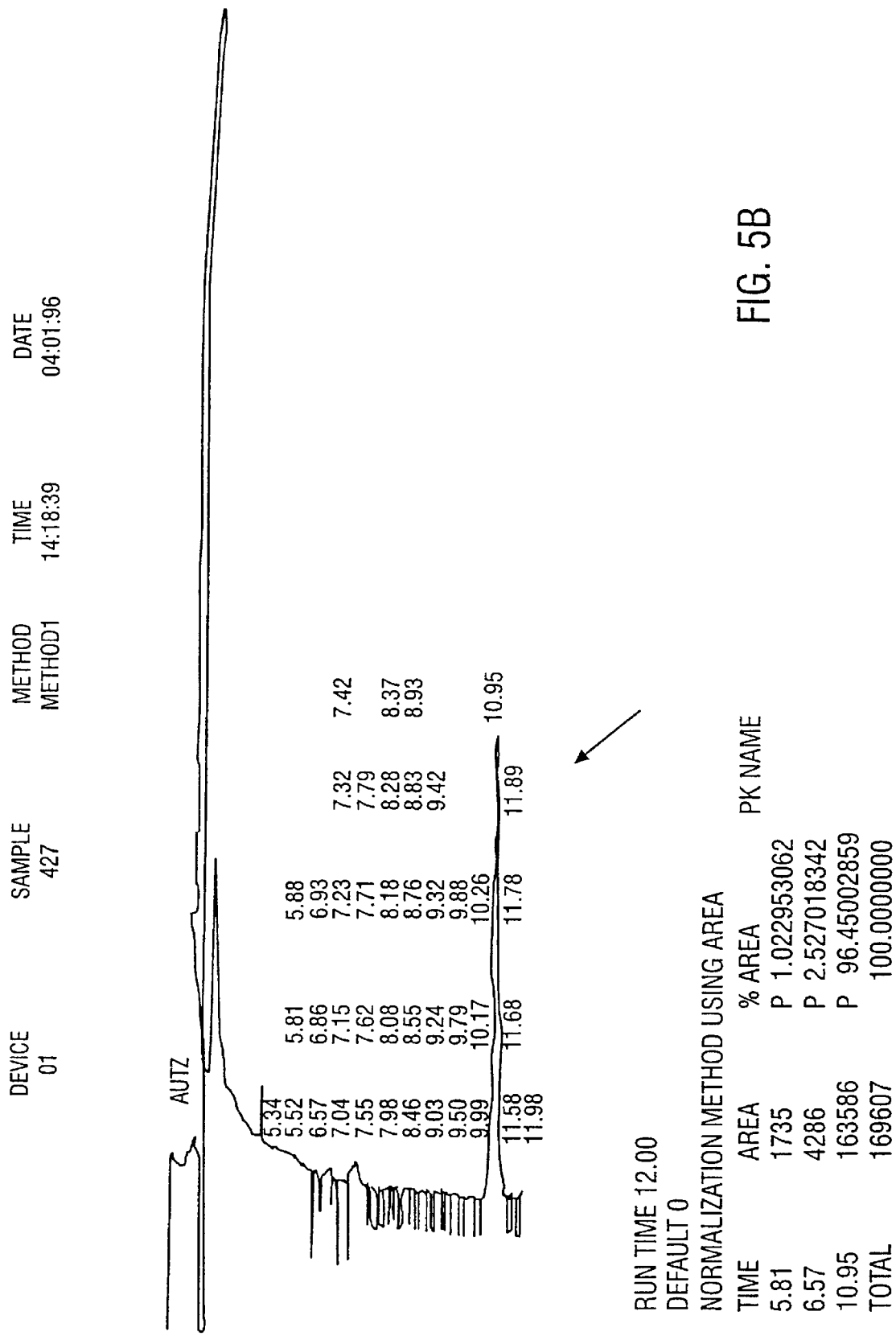
Figure 5C:
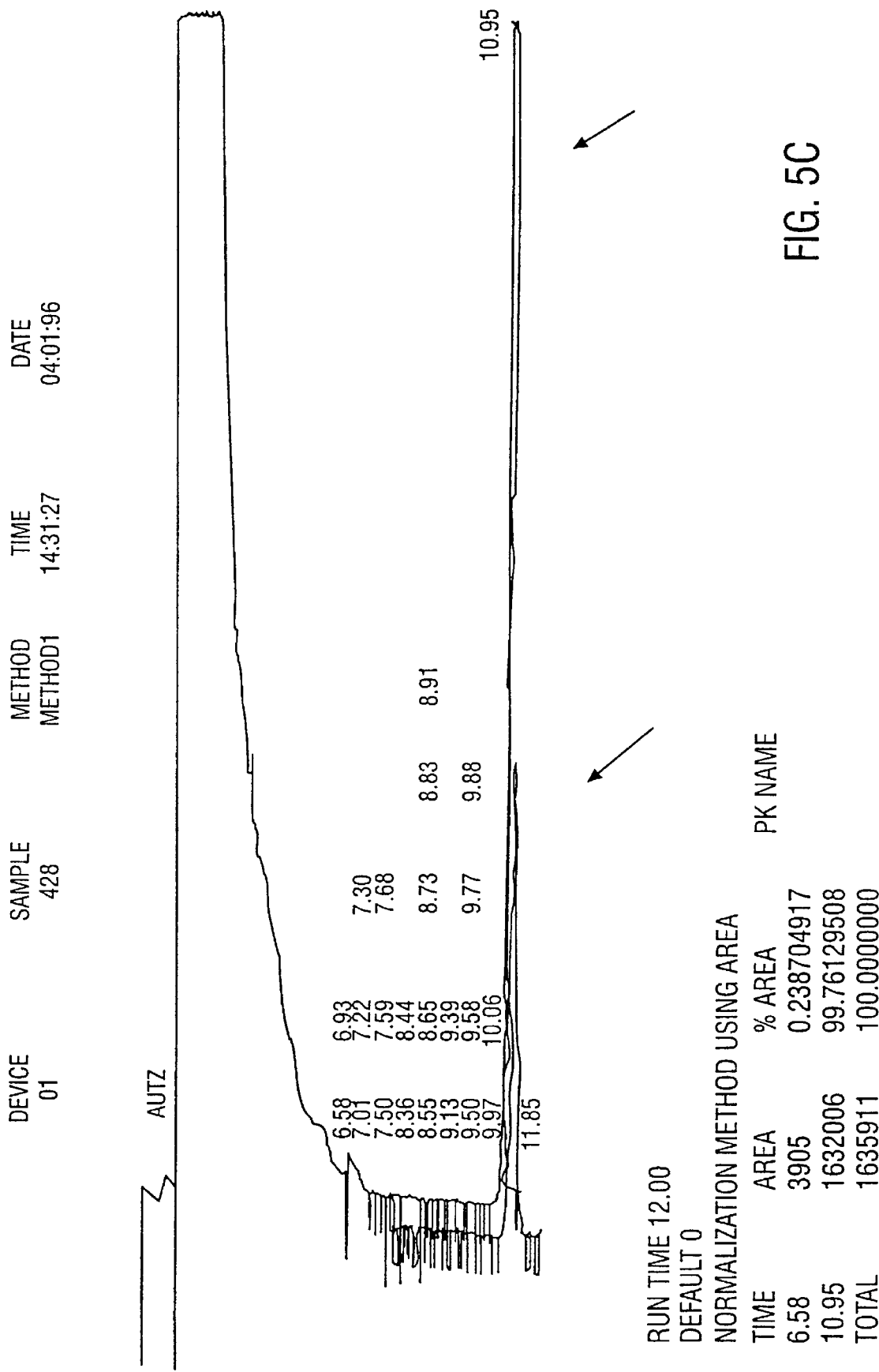

An example of authentic paclitaxel chromatograms from the HPLC assay is shown in FIG. 4 and FIG. 5. In this panel the drug was analyzed from the stability study using drug in the aqueous DMA/PEG/lipid "use" solvent. The retention time under the above conditions utilizing the $\mu$Bondapak phenyl column was about 17–18 min. After comparing alternative approaches, the $\mu$Bondapak phenyl column was exchanged for a $C_8$ Symmetry column, which gave identical recovery and sensitivity data, but with better resolution and a retention time in the range of only 10.3–11.3 min. The assay was linear from 10 ng/ml to 50.0 $\mu$g/ml in protein-free solutions, i.e., the various solvent systems utilized in the formulation-feasibility and -stability studies. This assay consistently yielded high recovery, accuracy and a lower sensitivity limit of about 5 ng/ml. The technique was standardized and used for all the stability studies without modifications. For the pharmacology study, the appearance of endogenous plasma protein peaks in the chromatogram necessitated the addition of an extraction/purification step. This extraction was accomplished with the Waters Sep Pak Vac 1 cc $tC_2$ extraction columns. For the results of the plasma analysis, see Example 3.

EXAMPLE 2

In Vitro Stability and Other Properties, a Preferred Formulation

Solubility Studies

An excess of paclitaxel as a powder was added to DMA, DMSO, PEG, and PG at RT. Each mixture was placed in a dark environment and checked visually for up to 1 hour for evidence of solubilization. Samples of 1 ml were taken at various time intervals, and filtered through a 0.45 $\mu$m PTFE™ membrane filter (Autovial®) fitted to a syringe assembly (Whatman Inc., Clifton, N.J.), and after appropriate dilution the paclitaxel concentration was determined by HPLC.

Stability of the Various Paclitaxel Formulations

To study the physical and chemical stability of the various parenteral formulations, 3 sets of studies were performed:

(a) Paclitaxel was dissolved at a concentration of 100 mg/ml in DMA only ("primary stock solution") and incubated at 4° C., 22° C., 40° C. and 60° C. Paclitaxel concentration were determined by HPLC in samples taken immediately after solubilization and in samples taken after gradually increasing time intervals of up to 48 hours.

(b) The DMA-paclitaxel mixture was diluted with PEG (1:3, v/v, DMA/PEG), or lipid emulsion (1:10 or 1:100, v:v, DMA:Intralipid, to yield a drug stock concentration in the range of 10–25 mg/ml.

(c) The DMA-paclitaxel mixture was diluted in normal saline or 5% dextrose in water to yield drug concentrations of 1 mg/ml and 5 mg/ml.

The various formulations were analyzed by HPLC immediately after mixing, then hourly for 8 hours, and then at gradually increasing time intervals for more than 10 days, depending on the initial rate of degradation in the respective solvent system.

The solubility of the drug differed markedly between different primary solvents. Only DMA and DMSO provided a solubility in excess of 100 mg/ml, and as described above, DMA was preferred for extended studies as the primary solvent.

To lower the DMA concentration in the final use-formulation and to improve the drug's shelf life, PEG was investigated as a cosolvent. The use of PEG was contemplated to allow subsequent dilution in an aqueous vehicle without drug precipitation or rapid chemical degradation, even at drug "stock" concentration as high as 25 mg/ml. In addition, the low overall DMA concentration in the complete solvent system was contemplated to yield a lower hemolytic potential of the final use-formulation than if a higher concentration of DMA or DMSO had been used in the primary solubilization step.

Osmotic Pressure Measurement

Osmotic pressures were measured with a micro-osmometer model 3moplus osmometer (Advanced Instruments Inc., Needham Heights, Mass.). The instrument was calibrated using Advans™ intrinsic calibration standards (Advanced Instruments Inc.) over a range of 500–2000 mOsm/kg. The test solution was placed in a disposable cuvette from the test kit and the osmotic pressure readings were recorded after equilibration in units of mOsm/kg. Triplicate measurements were carried out for each vehicle (without paclitaxel), and six measurements were done with paclitaxel added.

A two-tailed t test was used to evaluate the differences in osmotic pressure of the various vehicle formulations with and without the addition of paclitaxel (Mann and Whitney, 1947). The difference between the means of the two groups was to be considered significantly different for $P \leq 0.05$.

Hemolysis Studies In Vitro

The procedure of Parthasarathy et al. was used to examine the hemolytic potential of a few selected preparations and the $LD_{50}$ values of the most optimal formulation was constructed as described (Parthasarathy et al., 1994). Heparinized blood was mixed with an equal volume of Alsever's solution. This mixture was washed twice in PBS and a 10% (v/v) erythrocyte/PBS solution was then prepared and mixed with increasing amounts of the complete solvent system with or without the addition of paclitaxel. These mixtures were then incubated for 4 hours at 37° C. At the end of the incubation, the cells were pelleted at 10,000×g in an Eppendorf micro-centrifuge and the release of hemoglobin in the supernatant (ie., hemolysis) was determined spectrophotometrically at 550 nm. Maximum lysis was measured against a reference solution of erythrocytes that had been completely lysed by hypotonic shock. The hemolytic potential of the "optimal" complete formulation was evaluated as described (Parthasarathy et al., 1994) and the data were plotted as the fraction of healthy cells versus 1n (total volume percent). Total volume percent was defined as the volume percent of the vehicle in the mixture after dilution with blood. This was done to simulate the dilution of the respective drug formulation in the blood stream after parenteral administration. Healthy erythrocytes were defined as those capable of retaining their hemoglobin intracellularly after mixture with the solvent vehicle with or without paclitaxel (Parthasarathy et al., 1994).

In Vitro Cytotoxicity of Paclitaxel

The cytotoxic potential of selected solvent systems with and without paclitaxel was determined against the two human myeloid leukemia cell lines HL-60 (Gallagher et al., 1979) and KBM-7/B5 (Andersson et al., 1987; Andersson et al., 1995) using a previously published cytotoxicity assay, the "MTT" assay (Hansen et al., 1989; Andersson et al., 1995), and using a clonogenic assay (Andersson et al., 1994). HL-60 or KBM-7/B5 cells in Iscove's modified Dulbecco medium (IMDM) supplemented with 10% fetal bovine serum were incubated for 60 min at 37° C. Twenty-four hours later 25 μl MTT solution (5 mg/ml) (Sigma Chemicals, St. Louis, Mo.) was added to each sample and following an additional 2 hours of incubation at 37° C., 100 μl extraction buffer was added [extraction buffer: 20% (w/v) SDS dissolved to saturation at 37° C. in a solution of DMF and deionized water (1:1); pH 4.7]. After incubation overnight at 37° C., the optical densities were measured at 570 nm using a Titer-Tech™ 96-well multi-scanner™ against extraction buffer as the calibrating blank. The cytotoxicity was determined as the calorimetric difference between the samples exposed to solvent±paclitaxel as above and the background reactivity of cells that had been incubated in parallel in PBS alone. All determinations were performed in triplicate. Alternatively, after the 60 min incubation the cells were washed in ice-cold PBS, pH 7.4, and resuspended in IMDM with 20% fetal bovine serum and 0.3% agar as viscous support. After incubation for 7 days at 37° C., clones of >50 cells were counted under an inverted phase contrast microscope and survival curves were constructed as described (Andersson et al., 1994).

Equilibrium Solubility Determinations

A maximum equilibrium solubility of paclitaxel of >100 mg/ml was achieved in DMA and DMSO within 1 hour at RT. The solubility attempts utilizing PEG-400, PG, NS, Intralipid, and 5% dextrose respectively, did not yield any significant concentrations of solubilized drug (Table 1). The latter were therefore not further considered for study as primary solvents. In both DMA and DMSO, paclitaxel was completely stable for at least 4 hours at RT, but it is contemplated that the sulphur group of DMSO could be reactive with the taxane structure upon extended exposition at RT. Anhydrous DMA was therefore favored as the primary solvent. When a paclitaxel solubility of >100 mg/ml had been reached in DMA, the drug started degrading slowly after storage over night at RT. To stabilize the agent, several cosolvents were examined. When PEG was used in combination with DMA, real life stability studies at 4° C. and at RT yielded no discernible degradation over more than 4.5 months (FIG. 1).

Stability Studies of the Various Formulations

Figure 2:
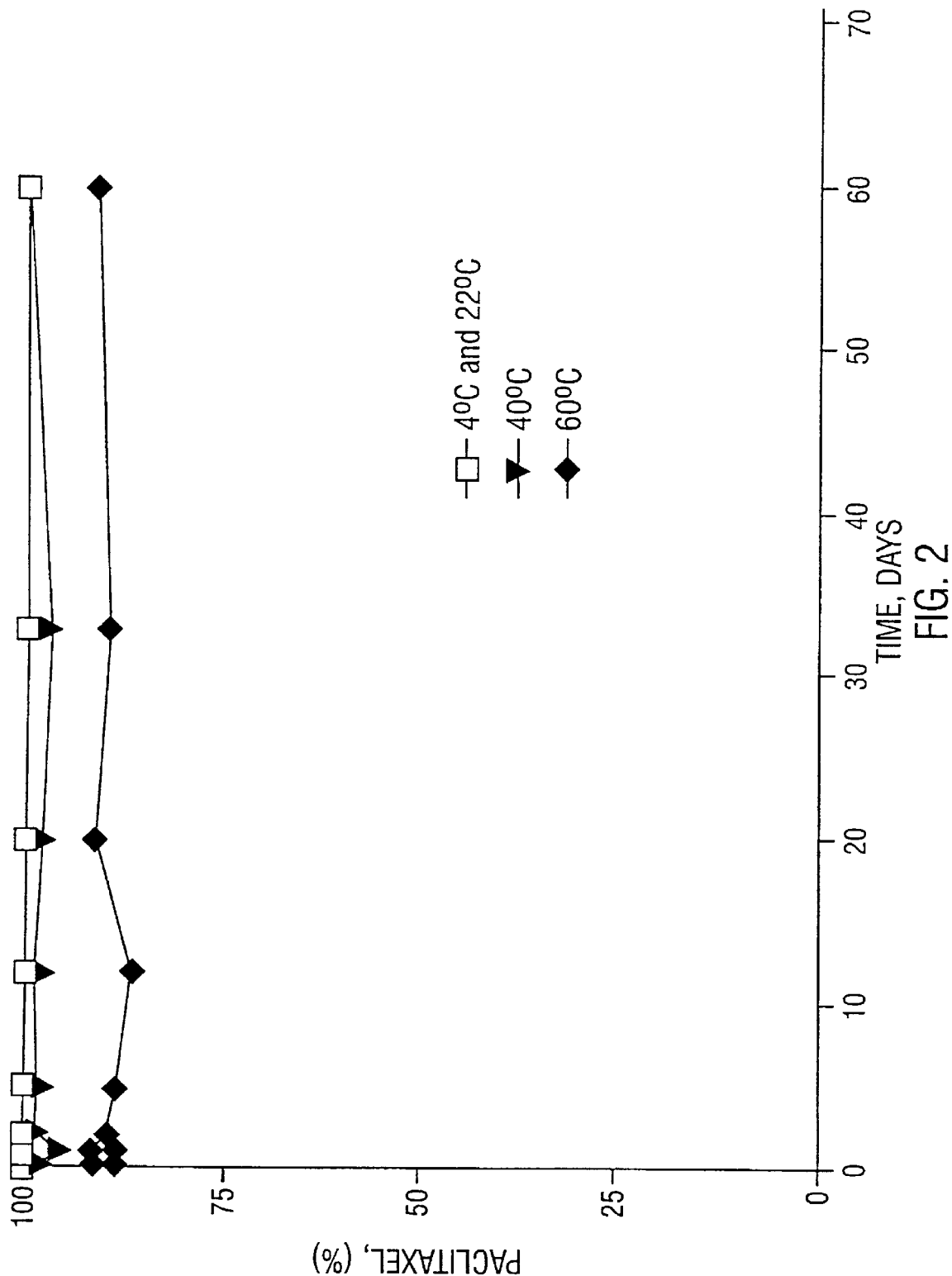
FIG. 2. Accelerated stability study of paclitaxel in the DMA:PEG (1:3, v/v) stock formulation at a concentration of 25 mg/ml, at 4° C., at room temperature (RT, 22° C.), at 40° C., and at 60° C. The stability curves obtained for the samples at 4° C., and at RT were overlapping at 100% for the entire 60 day observation period.
Figure 3:
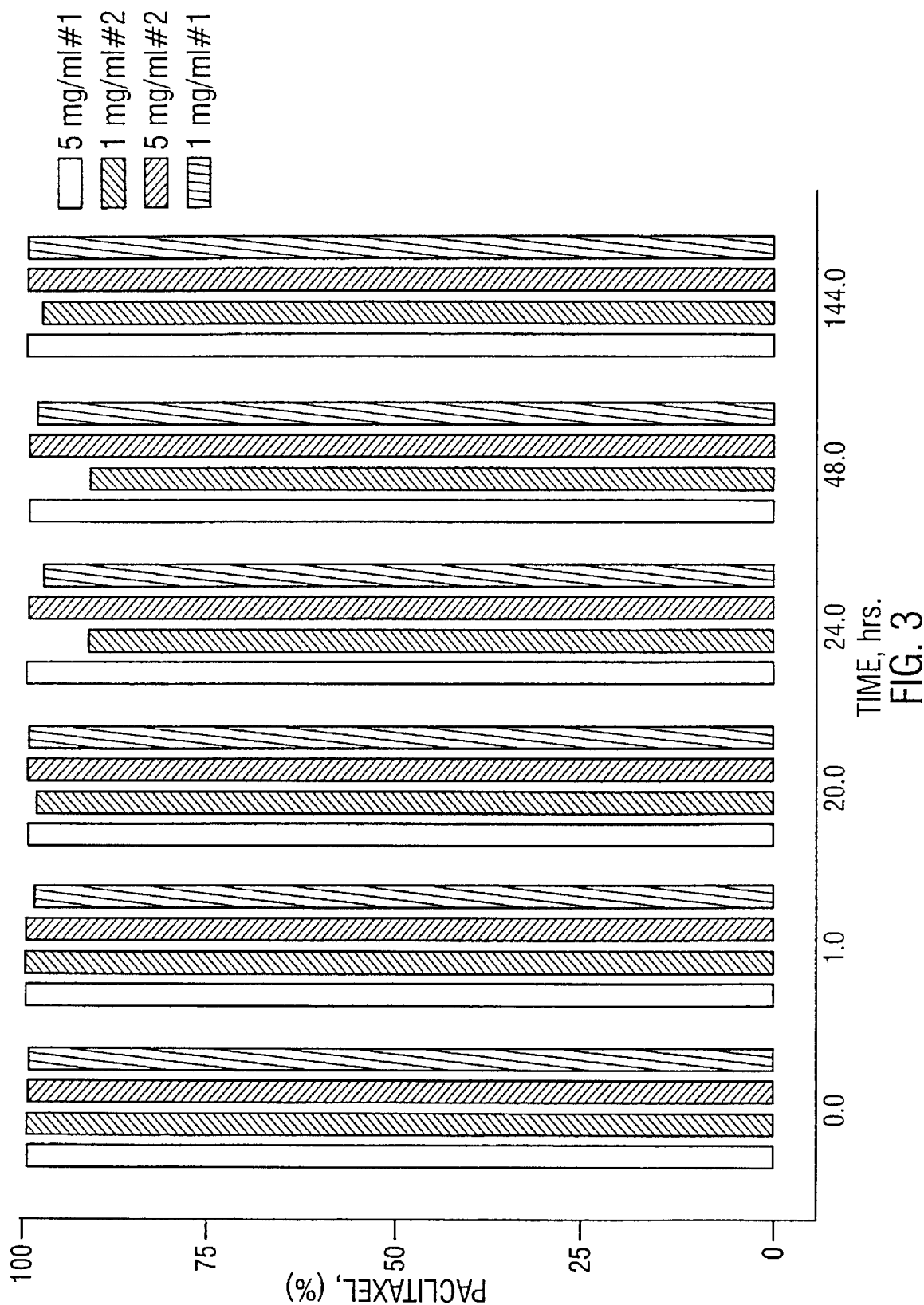
FIG. 3. Stability of paclitaxel at RT in the final use-formulation of DMA/PEG (1:3, v/v), then further diluted with Intralipid to 1 mg/ml, and to 5 mg/ml. Two different lots of solubilized paclitaxel were prepared and tested in parallel.

The temperature-dependent stability of solubilized paclitaxel in the different solvent formulations was studied as follows: The drug was dissolved in DMA at 100 mg/ml and after addition of PEG (1:3, v/v), to a final paclitaxel concentration of 25 mg/ml. Different aliquots were stored at 4° C., 22° C., 40° C., and 60° C. (FIG. 2). Immediately after solubilization and at various intervals up to more than 50 days, aliquots from different samples were analyzed by HPLC. The drug samples stored at 4° C., at RT, and at 40° C. did not show any significant degradation over the first 60 days of observation. At 60° C. there was a loss of about 10–15% in the first 6 hours of observation, after which there appeared to be no further degradation for more than 6 weeks. The findings suggest that the drug is also stable at elevated temperatures in this stock formulation.

When NS or 5% dextrose in water were then used as the final solvents, significant degradation took place within 4–6 hours. In contrast, when an aqueous lipid emulsion was used as the terminal solvent vehicle, the resulting solution was stable at 1 mg/ml and at 5 mg/ml for over one week at 4° C. and at RT, see FIG. 3.

Osmotic Pressure

It is desirable that a parenteral formulation of a pharmacologically active agent be isosmotic to blood. A hypertonic delivery system can be utilized if the drug/solvent is infused through a (central) venous catheter and gradually diluted in a large blood volume. The osmotic pressure of one of the current formulations is shown in Table 2. The primary DMA/PEG-stock formula with or without paclitaxel was very hypertonic; its osmotic pressure was estimated at more than 4,000 mOsm/kg, as compared with 280–295 mOsm/Kg for human blood. In contrast, the mixture of DMA/PEG/paclitaxel with Intralipid was closer to isosmotic. The osmolarity of this complete vehicle was not appreciably changed by the addition of paclitaxel at 1 mg/ml (<5%).

Hemolysis

Figure 6:
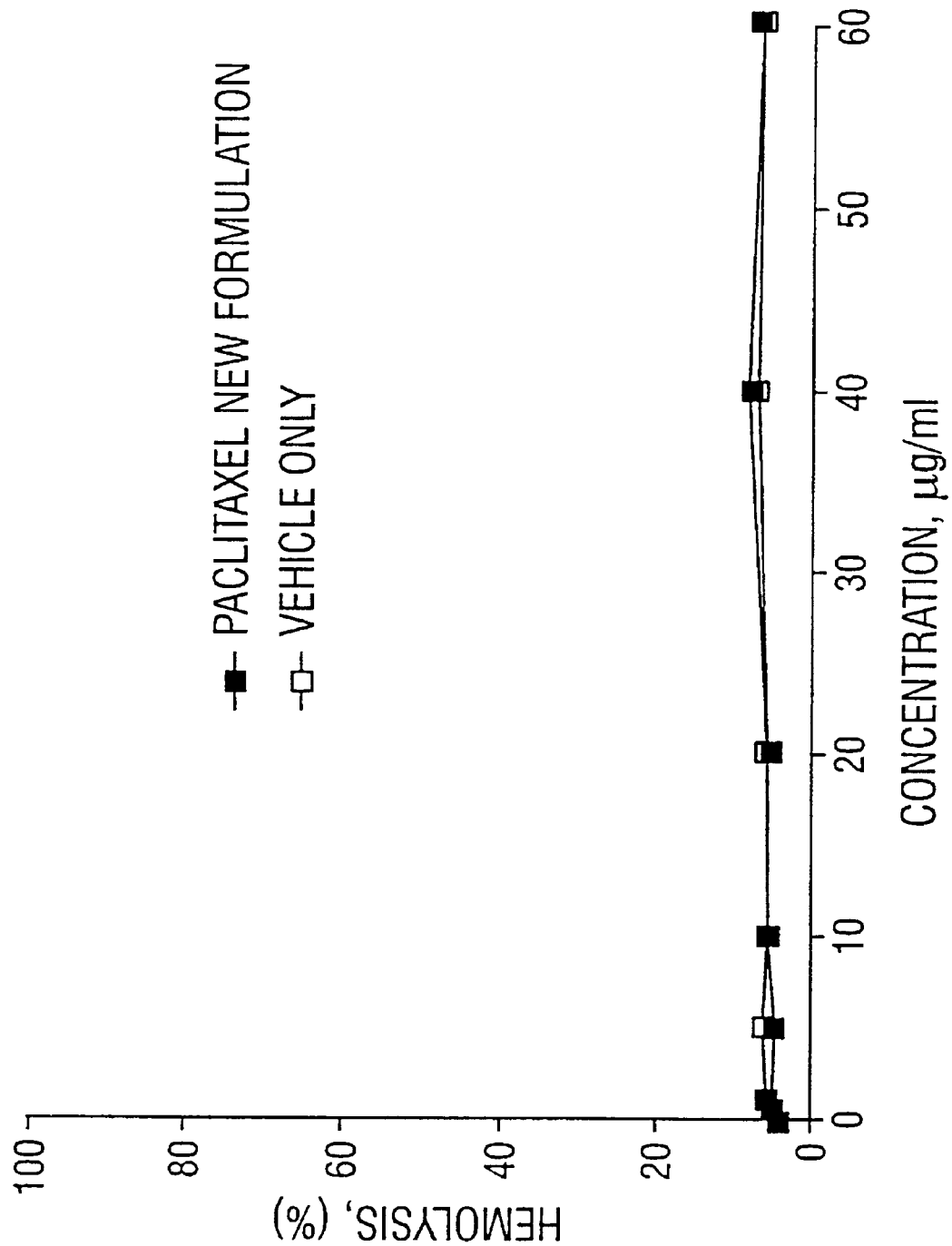
FIG. 6. Hemolytic potential of the final use formulation of DMA:PEG:Intralipid without (□), and with paclitaxel (■), respectively.

As shown in FIG. 6, the use-formulation showed a low capacity for inducing hemolysis when the complete vehicle was used either with or without the addition of paclitaxel. The paclitaxel dependent lysis was barely notable above background for drug concentrations up to and exceeding 50 $\mu$g/ml. The taxane-specific hemolysis was highly reproducible between different studies. The details from the different studies using the complete use-vehicle with and without paclitaxel are summarized in FIG. 6. The DMA/PEG/Intralipid™ formulation had a very low hemolytic potential.

In Vitro Cytotoxicity of Paclitaxel

Figure 7:
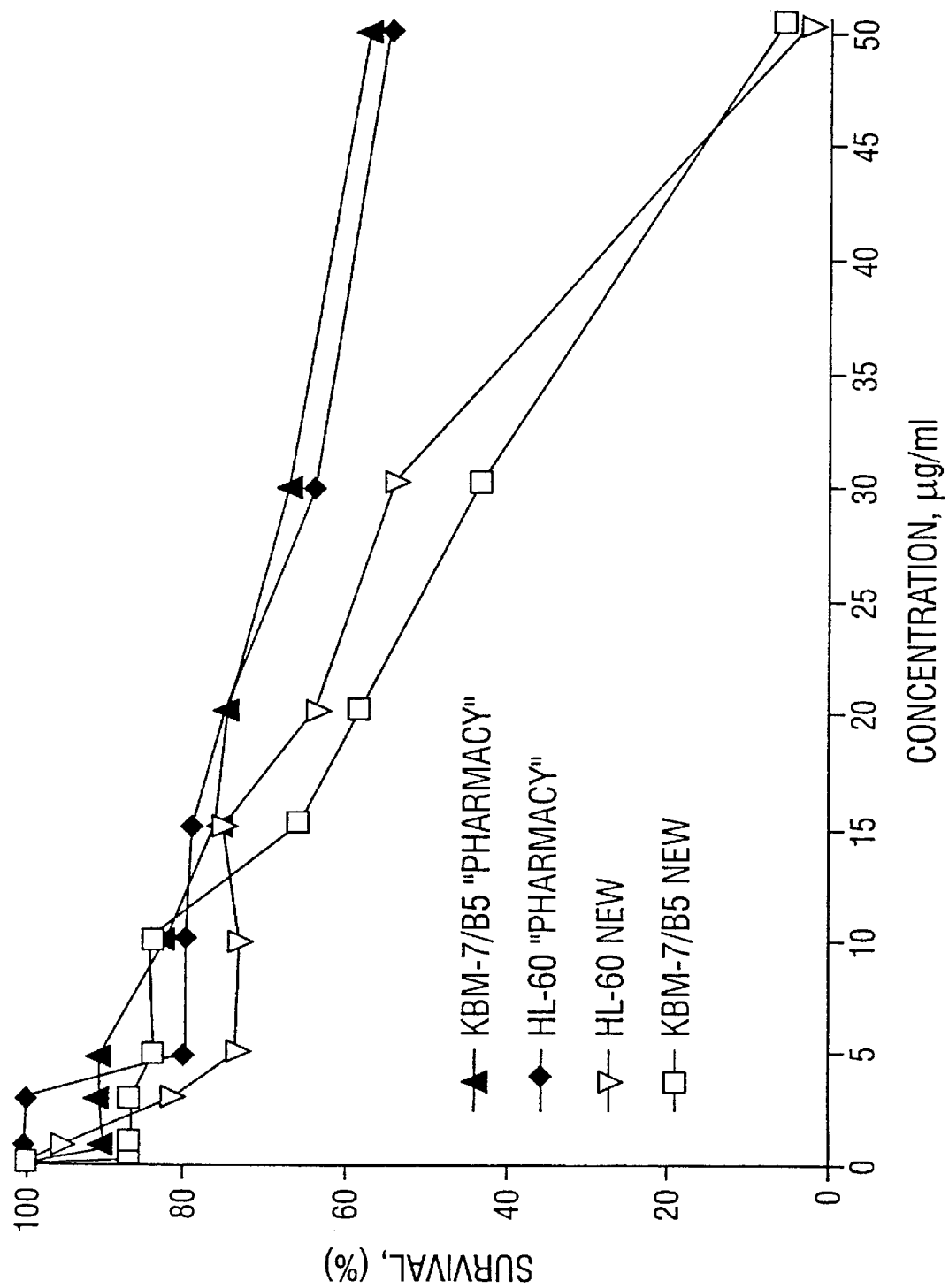
FIG. 7. Cytotoxic activity of paclitaxel in the DMA:PEG:Intralipid use-formulation against the two human cell lines KBM-7/B5 and HL-60 assessed with the clonogenic assay after a 60-minute drug exposure. As a positive control served paclitaxel in the commercially available preparation. For details see Example 2 in the text.

The HL-60 and KBM-7/B5 myeloid cells were exposed to paclitaxel in the terminal use vehicle of DMA/PEG/Intralipid at increasing volume ratios with or without the addition of increasing drug concentrations and as a positive control for paclitaxel in the Cremophor® EL/ethyl alcohol formulation. None of these solvent systems had any detectable toxicity by themselves against the cell lines used in these studies with the MTT or in the clonogenic assay. When paclitaxel was added to the respective solvent system, a concentration dependent cytotoxicity was observed with both formulations (see FIG. 7 for the data obtained with the clonogenic assay; analogous, confirmatory data were obtained with the MTT assay). It appears that the drug retained at least an equivalent cytotoxic potential in the examined novel formulation as compared with the standard formulation.

EXAMPLE 3

Quantitative Paclitaxel Analysis in Plasma and Pharmacology of iv Paclitaxel

Quantitative Extraction of Paclitaxel in Plasma

Rat plasma (500 $\mu$l) was mixed with various amounts of paclitaxel (in <3% of the final volume) to yield a drug concentration of 0.05–3.0 $\mu$g/ml (from a paclitaxel stock use-solution in DMA/PEG/Intralipid at a drug concentration of 5 mg/ml). The drug was extracted from the plasma samples as described above. 500 $\mu$l plasma was loaded on to Sep Pak Vac 1 cc to tC2 cartridges that had been preconditioned with 1 ml MeOH and then 1 ml water. Subsequently, the sample was washed with 1 ml water followed by 1 m MeOH:water (1:3, v/v), then eluted with 500 $\mu$l MeOH:water (85:15, v/v). The eluate was subjected to HPLC analysis as described above and paclitaxel was spectrophotometrically detected at 227 nm. The paclitaxel recovery from rat plasma spiked to a drug concentration of 10 $\mu$g/ml was calculated to be 87±3%. The assay was linear in the interval from 10 ng/ml to 50 $\mu$g/ml with a detection limit of 5 ng/ml.

Parenteral Paclitaxel in Rats

For the in vivo study, male Sprague-Dawley rats with a body weight of 250–300 g were used. They were bought from the Harlan-Sprague-Dawley local breeding facility in Houston, Tex. The animals were allowed a minimum of 3–4 days to accommodate to the change of environment after shipping to the MD Anderson Cancer Center. All animals were allowed free access to commercial feed and tap water prior to and during the pharmacological study. The dose of 3 mg/kg was determined as the highest dose that could be given to the rats as a slow iv injection of the Cremophor® EL based preparation without a lethal anaphylactoid reaction in the absence of pharmacological premedication. Attempted injection of 5 mg/kg and 10 mg/kg body weight resulted in sudden death from anaphylaxis when the Cremophor® EL based formulation was used, but not when the disclosed formulation was used.

For the in vivo pharmacology study, the paclitaxel was formulated in DMA/PEG to a stock drug concentration of 25 mg/ml and then diluted with Intralipid so the dose (3.0 mg/kg) could be administered iv in a maximum volume of 0.5 ml by injection through a tail vein. Contrary to the manufacturer's recommendations for the commercially available paclitaxel preparation (TAXOL® (Paclitaxel)), no pharmacologic premedication was used for the animals in the present study. This avoided the possible influence of induction of microsomal liver enzymes which could alter drug metabolism/elimination and influence (the later part of) the plasma concentration curve. For the same reason, all animals were unanesthesized and only physically restrained during the drug injection. The drug concentration of the injected use-formulation was confirmed by HPLC prior to use. Blood samples of 0.5–1.0 ml were drawn in heparinized tubes through cardiac puncture under light $CO_2$ anesthesia prior to drug infusion (for blank plasma), and at selected time points from 5 min up to 24 hours after the injection for determination of paclitaxel plasma concentrations. The blood was centrifuged at 1,000×g for 10 min and the plasma was separated and stored at −80° C. until extracted and assayed by HPLC as described above.

Paclitaxel in Plasma and iv Drug Pharmacology

Figure 8A:
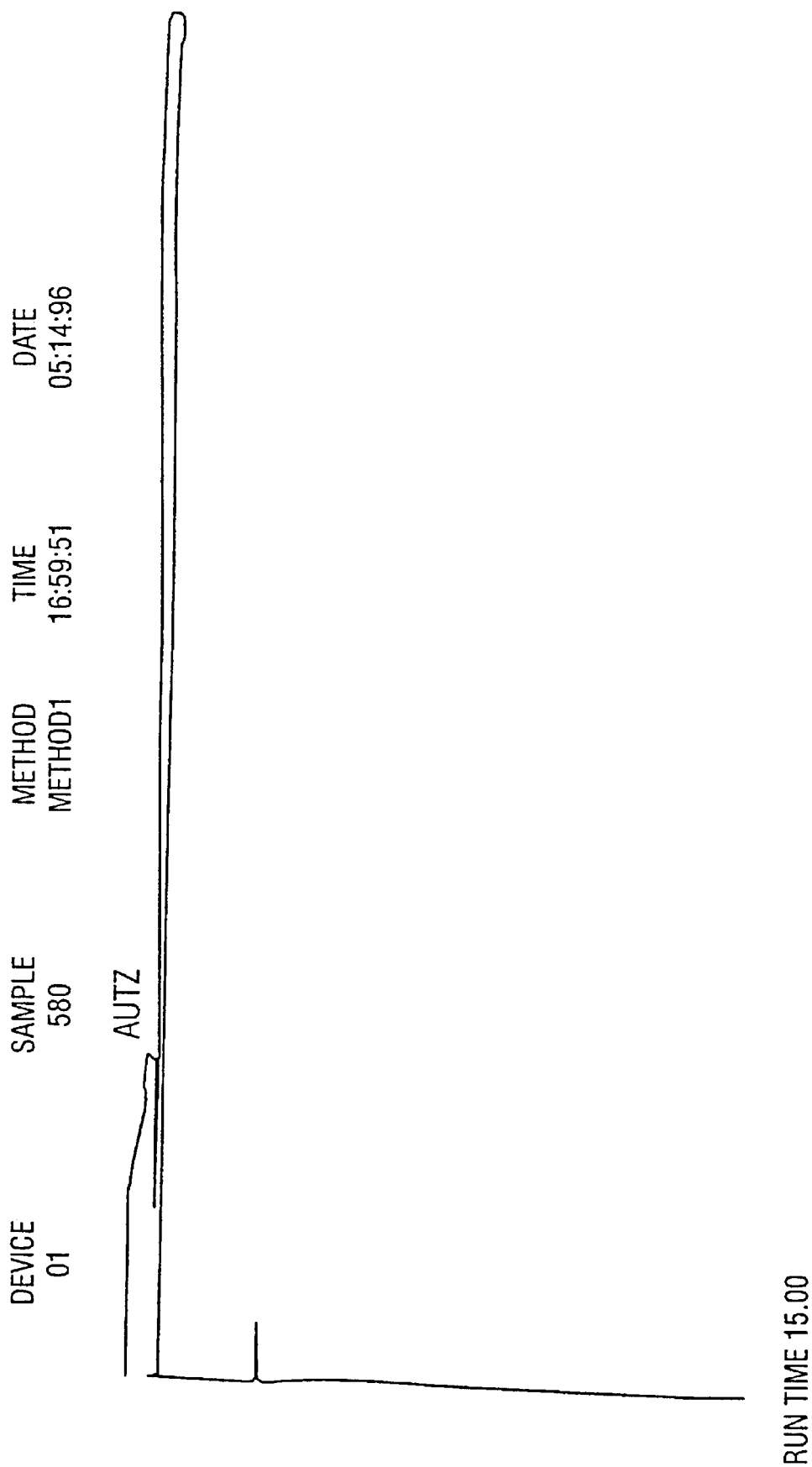
FIG. 8. Chromatograms of plasma samples extracted with the SepPak cartridge as described under Example 3 (pages 23–24) prior to HPLC; a) blank plasma, b) plasma spiked with paclitaxel in the new formulation to 10 μg/ml, and c) an authentic chromatogram from the pharmacology study, where rats were injected with 3 mg/kg of the drug. This blood sample was obtained 5 min after injection.
Figure 8B:
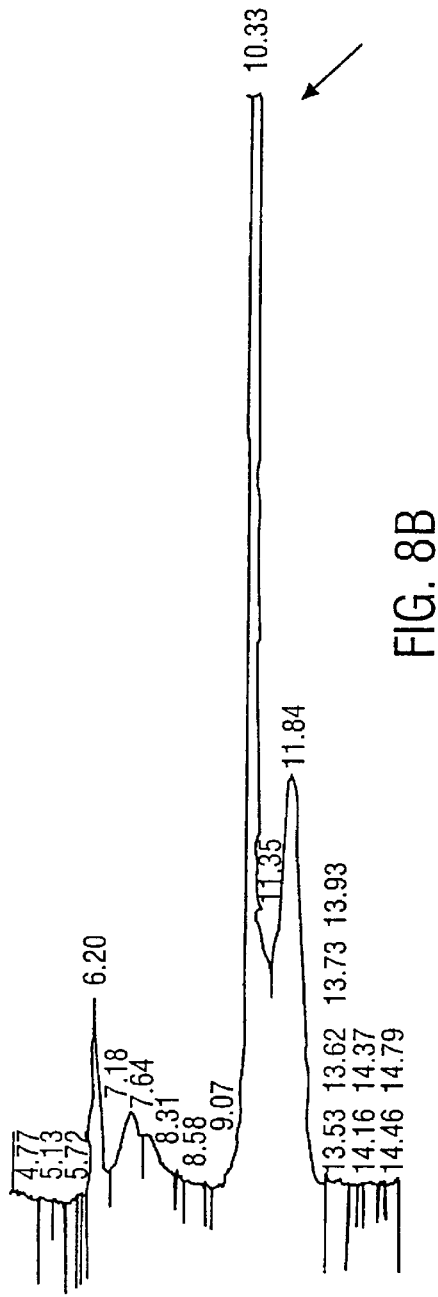
Figure 8C:
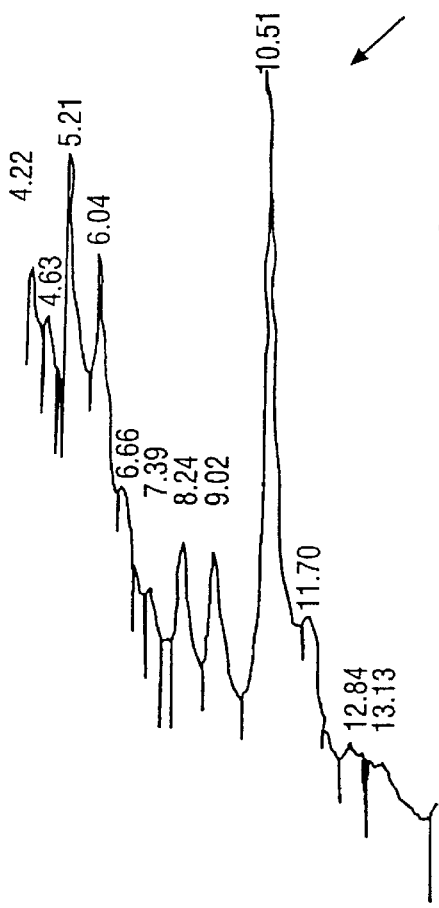

The drug extraction from plasma with MeOH using the Sep Pak Vac 1 cc $tC_2$ columns was essential to avoid interference from endogenous plasma components and to recover the maximum amount of drug. Authentic chromatograms from blank plasma, paclitaxel-spiked plasma, and one example of that obtained after extraction of a plasma sample from the current pharmacokinetic study are shown in FIG. 8. The paclitaxel retention time in this system was 10.3–11.3 min. The recovery of paclitaxel with the above described technique was 87±3% when rat plasma was spiked in vitro with 10 $\mu$g/ml of drug. The assay was linear after drug extraction from plasma samples in the range from 10 ng/ml to 50 μg/ml. The limiting sensitivity was about 5 ng/ml when 200 μl was injected in the chromatograph. It is contemplated that this sensitivity may be improved by utilizing a larger part of the 2 ml injection loop of the system and also by evaporating/reconstituting the 500 μl eluate in a smaller volume. A standard curve was prepared in the concentration range from 10 ng/ml to 1,000 ng/ml for the pharmacology study and a good correlation was obtained between the plasma paclitaxel concentration and peak AUC value.

Figure 9:
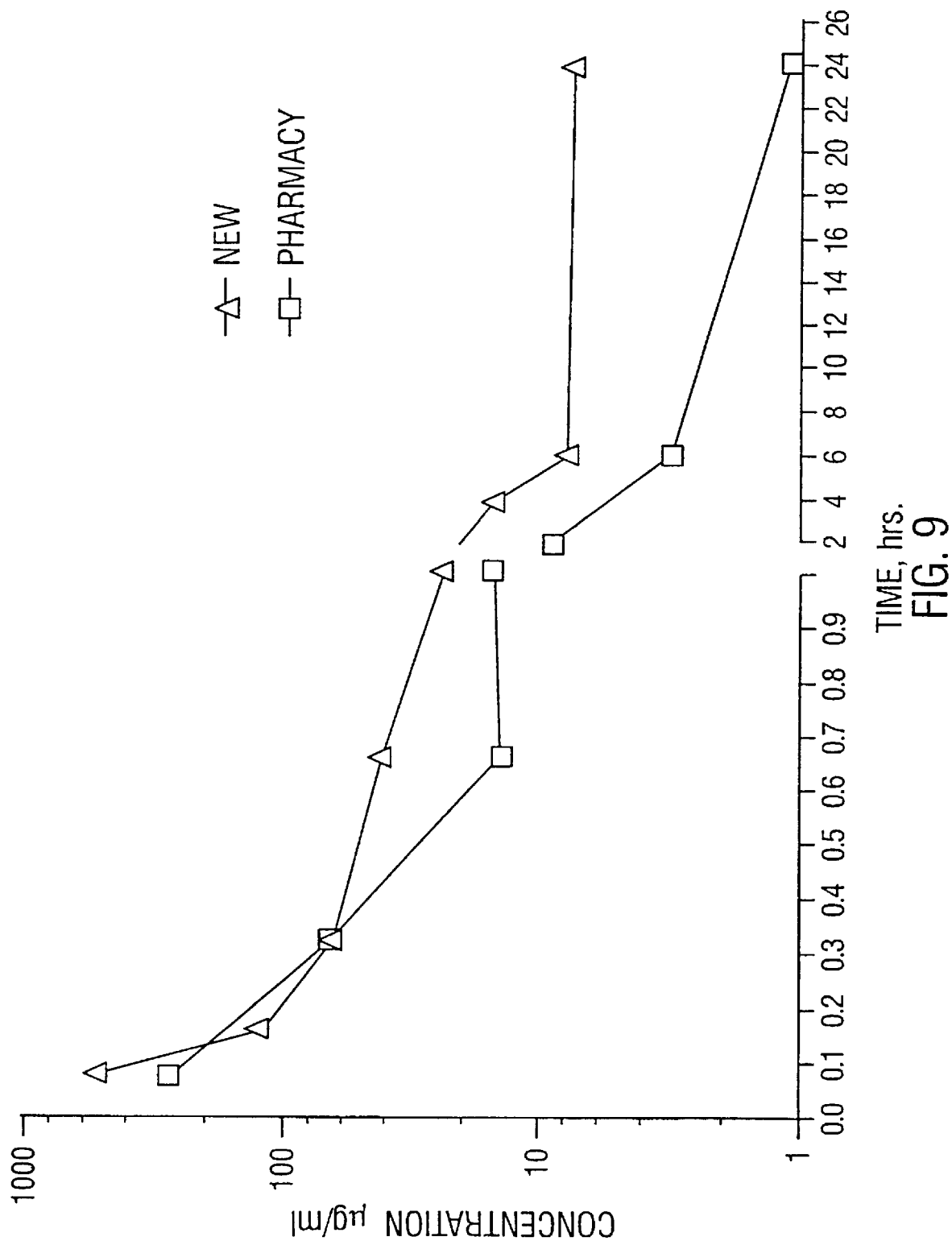
FIG. 9. Plasma concentration vs. time pattern of paclitaxel injected at 3 mg/kg in male Sprague-Dawley rats (-Δ- new formulation, DMA:PEG:Intralipid). As positive controls rats were injected with the commercially available preparation (□).

The data illustrate that the novel paclitaxel formulation gives at least equivalent plasma concentrations to those obtained after the injection of an identical dose of 3 mg/kg body weight of the commercially available preparation (FIG. 9).

Taken as a whole, the present examples demonstrate the successful design of pharmaceutically acceptable, stable formulations of taxane analogs, using paclitaxel as the prototype compound. The optimal solvent system is physiologically compatible with intravascular administration with good tolerance and negligible acute solvent system toxicity, as shown in the rodent model. The intravascular injection of one of the preparations in rats (3.0 mg/kg similar to 200 mg/m$^{-2}$ of body surface area), yielded plasma concentrations that reached, and over many hours, maintained cytotoxic concentrations of paclitaxel. It should be noted, that for this study a formulation of 1:3 mixture of DMA and PEG, with Intralipid as the "terminal" solvent for the use-formulation was used.

The data obtained with the preferred final use-formulation, DMA/PE/Intralipid, demonstrate conclusively the feasibility of introducing this parenteral taxane (paclitaxel) formulation in clinical therapy of malignant disease, with the predictable attainment of cytotoxic activity and with a reasonable expectation of low or negligible normal organ toxicity from the solvent vehicles. In particular, the possibility of serious life-threatening hypersensitivity reactions, which may at least in part be connected with the use of large amounts of iv Cremophor® EL and ethyl alcohol can now be completely avoided. These novel solvent systems are contemplated to not only dramatically reduce the risk of solvent system toxicity, but also to minimize the risk that the organic solvents could potentiate clinically adverse effects related to taxane analogs, such as e.g., paclitaxel, and allow for convenient handling and accurate evaluation of prolonged administration schedules.

SUMMARY

Novel vehicles have been invented for the stable, pharmaceutically acceptable formulation of lipophilic taxane analogs such as paclitaxel for intravascular administration. A sensitive and specific HPLC assay was developed, which allowed the reproducible quantitation of paclitaxel concentrations as low as 10–50 ng/ml. In parallel, extraction techniques were developed to reproducibly recover paclitaxel from plasma samples procured after its intravascular administration. Thereafter, stability studies of the newly formulated parenterally compatible vehicles were initiated to select the best formulation for studies of hemolytic potential and in vitro cytotoxic activity. Subsequently, one of the stable new formulations was injected parenterally in rats at 3.0 mg/kg body weight. It is apparent from the presented results, that high drug concentrations can be obtained after iv injection of the novel preparation in the rat model. Further, this preparation yielded plasma drug concentrations and areas under the plasma concentration vs. time curves that clearly were in the cytotoxic range. It should now be possible to study these most stable, low-toxicity vehicles containing taxanes such as paclitaxel for parenteral treatment of metastatic cancer. Ultimately, clinical studies of the efficacy of paclitaxel and other taxane analogs against malignant disease will be performed.

TABLE 1

Solubility of Paclitaxel in Various Solvents

| Solvent | Number of Experiments | Solubility, mg/ml |
|---|---|---|
| DMA | 3 | >200 |
| DMSO | 1 | >100 |
| Propylene glycol | 1 | insoluble[a] |
| PEG | 1 | insoluble |
| Normal saline | 1 | insoluble |
| 5% dextrose | 1 | insoluble |
| Intralipid ™ | 1 | insoluble |

[a]Insoluble is here defined as a solubility of <0.1 mg/ml after 60 min at room temperature

TABLE 2

Osmotic Pressures of One New Paclitaxel Formulation

| Solution | n[a] | Osmotic Pressure, mOsm/kg (±S.D.) |
|---|---|---|
| New stock formulation DMA:PEG(1:3) | 1 | >4,000[b] |
| New use formulation[c], vehicle only | 3 | 568 ± 7 |
| New use-formulation[d], vehicle with paclitaxel | 3 | 592 ± 10 |
| 5% Dextrose in water | 3 | 286 ± 12 |
| Normal Saline | 3 | 233–238 |
| Blood | 8 | 280–295 |
| Water | 3 | 3 | n[a], the number of independent observations
[b], this experimental value is probably artifactual; the osmometry uses freeze point depression, which may not truly reflect the physical properties of organic solvents under physiological conditions
[c], the formulation was the DMA:PEG:Intralipid use-formulation described in the text
[d], the formulation was the above use-formulation, the paclitaxel concentration 1.0 mg/ml While the compositions and methods of this invention have been described in terms of preferred embodiments, it will be apparent to those of skill in the art that variations may be applied to the compositions, methods and in the steps or in the sequence of steps of the methods described herein without departing from the concept, spirit and scope of the invention. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Rowinsky E K, Cazenave L A, Donehover R C, "Taxol: A Novel Investigational Antimicrotubule Agent," *J National Cancer Institute*, 82:1247–1259, 1990.

Nicoletti M I, Lucchini V, Massazza G, Abbott, B J, D'Inaclei M, and Giavazzi R, "Antitumor Activity of Taxol (NSC-125973) in Human Carcinomas Growing in the Peritoneal Cavity of Nude Mice," *Annals of Oncology*, 4:151–155, 1993.

Rose W C, "Taxol-Based Combination Chemotherapy and Other In Vivo Preclinical Antitumor Studies," *Monogr National Cancer Institute*, 15:47–53, 1993.

Verweij J, Clavel M, Chevalier B, "Paclitaxel (Taxol™ and docetaxel (Taxotere™) "Not Simply Two of a Kind," *Annals of Oncology,* 5:495–505, 1994.

Rowinsky E K, McGuire W P, Donehower R C, "The Current Status of Taxol. *In: Principles and Practice of Gynecologic,"* Hoskins W J, Perez C A, Young R C (Eds), *Oncology Updates,* J. B. Lippincott Company Philadelphia, Pa., 1993.

Brown T, Haviin K, Weiss G, Cagnola J, Koeller J, Kuhn J, Rizzo J, Craig J, Phillips J, von Hoff D, "A Phase I Trial of Taxol Given by a 6-Hour Intravenous Infusion," *J Clin. Oncology,* 9:1261–1267, 1991.

Holmes F A, Walters R S, Theriault R L, Forman A D, Newton L K, Raber M N, Buzdar A U, Frye D K, Hortobagyi G N, "Phase II Trial of Taxol, An Active Drug in the Treatment of Metastatic Breast Cancer," *J National Cancer Institute,* 83:1797–1805, 1991.

Seidman A D, Reichman B S, Crown J P A, Yao T-J, Currie V, Hakes T B, Hudis C A, Gilewski T A Baselga J, Forsythe P, Lepore J, Marks L, Fain K, Souhrada M, Onetto N, Arbuck S, Norton L, "Paclitaxel as Second and Subsequent Therapy for Metastatic Breast Cancer: Activity Independent of Prior Anthracycline Response," *J Clin. Oncology,* 13:1152–1159, 1995.

Chevallier B, Fumoleau P, Kerbrat P, Dieras V, Roche H, Krakowski I, Azli N, Bayssass M, Lentz Mass., Van Glabbeke M, "Docetaxel is a Major Cytotoxic Drug for the Treatment of Advanced Breast Cancer: A Phase II Trial of the Clinical Screening Cooperative Group of the European Organization for Research and Treatment of Cancer," *J Clin. Oncol.,* 13:314–322, 1994.

Weiss R, Donehower R C, Wiemick P H et al., "Hypersensitivity Reactions from Taxol," *J Clin. Oncology,* 8:1263–1268, 1990.

TAXOL® (Paclitaxel) for injection concentrate. Product insert label from Mead-Johnson, a subsidiary of Bristol Meyers Squibb, Inc.

Spiegel A J, and Noseworthy M N, "Use of Nonaqueous Solvents in Parenteral Products," *J Pharm. Sci.,* 52:917–927, 1963.

Yalkowsky S H and Roseman T J, "Solubilization of Drugs by Cosolvents. *In: Techniques of Solubilization of Drugs,"* Marcel Dekker Inc., New York, N.Y., pp. 91–134, 1981.

U.S. Department of Health and Human Services: NCI Investigational Drugs. NIH Publication No. 84–2141, 1984.

Weiss A J, Jackson L G, Carabasi R A, Mancall E L, White J C, "A Phase I Study of Dimethylacetamide," *Cancer Chemother. Rep.,* 16:477–85, 1962.

Kim S N, "Preclinical Toxicology and Pharmacology of Dimethylacetamide with Clinical Notes," *Drug Metab. Rev.,* 19:345–368, 1988.

Lockard J S, Levy R H, Congdon W C, DuCharme L L, "Efficacy and Toxicity of the Solvent Polyethylene Glycol 400 in Monkey Model," *Epilepsia,* 20:77–84, 1979.

Keating M J, Holmes R, Lemer S, Ho DH, "L-Asparaginase and PEG Asparaginase-Past, Present and Future," *Leukemia and Lymphoma,* 10:153–57, 1993.

Davis J M and Rowley S D, "Autologous Bone Marrow Graft Processing. *In: Processing of Bone Marrow for Transplantation,* Sacher Ra, McCarthy L J, Smit Siblinga Cth, American Association of Blood Banks, Arlington, Va. pp. 41–62, 1990.

Gorin N C, "Cryopreservation and Storage of Stem Cells. In: Bone Marrow and Stem Cell Processing: *A Manual of Current Techniques,"* Areman E M, Deeg J H, Sacher R A, pp. 292–362, 1992.

Fortner C L, Grove W R, Bowie D, Walker M D, "Fat Emulsion Vehicle for Intravenous Administration of an Aqueous Insoluble Drug," *Am. J Hosp. Pharm.,* 32:582–84, 1975.

Rizzo J, Riley C, von Hoff D, "Analysis of Anticancer Drugs in Biological Fluids: Determination of Taxol with Application to Clinical Pharmacokinetics," *J: Pharmaceut. Biomed. Anal.,* 8:159–164, 1990.

Willey T A, Bekos E J, Gaver R C, Duncan G F, Tay L K, Beijnen, Framen R H, "High-Performance Liquid Chromatographic Procedure for the Quantitative Determination of Paclitaxel (Taxol®) in Human Plasma," *J Chromatography,* 621:231–238, 1993.

Sharma A, Conway W D, Straubinger R M, "Reversed-Phase High-Performance Liquid Chromatographic Determination of Taxol in Mouse Plasma," *J Chromatography B,* 655:315–319, 1994.

Eiseman J L, Eddington N D, Leslie J, MacAuley C, Sentz D L, Zuhowski M, Kujawa J M, Young D, Egorin M J, "Plasma Pharmacokinetics and Tissue Distribution of Paclitaxel in $CD_2F1$ Mice," *Cancer Chemother. Pharmacol,* 34:465–471, 1994.

Unpublished Method: Courtesy of Xechem Inc., Newark, N.J.

Mann H B and Whitney D R, "On a Test Whether One of Two Random Variables is Stochastically Larger than the Other," *Ann. Math. Statist.,* 18:50–60, 1947.

Parthasarathy R, Sacks P G, Harris D, Brock H, Metha K, "Interaction of Liposome-Associated All-Trans-Retinoic Acid with Squamous Carcinoma Cells," *Cancer Chemother. Pharmacol.,* 34:527–34, 1994.

Gallagher R, Collins S, Trujillo J, McCredie K B, Ahearn M, Tsai S, Anlakh G S, Ting R, Ruscetti F, Gallo R, "Characterization of the Continuously Differentiating Myeoloid Cell Line (HL-60) from a Patient with Acute Promyelocytic Leukemia," *Blood,* 54:254–68, 1979.

Andersson B S, Beran M, Pathak S, Goodacre A, Barlogie B, McCredie K B, "Ph-Positive Chronic Leukemia with Near-Haploid Conversion In Vivo and Establishment of a Continuously Growing Cell Line with Similar Cytogenetic Pattern," *Cancer Genetics and Cytogenet,* 24:335–43, 1987.

Andersson B S, Collins V P, Kruzrock R, Larkin D W, Childs C, Ost A, Cork A, Trujillo J M, Beran M, Freirech E J, Siciliano M and Deisseroth A B, "KBM-7; Human Myeloid Leukemia Cell Line with Double Philadelphia Chromosomes but Lacking Normal BCR and c-ABL Transcripts," *Leukemia,* 9:2100–2108, 1995.

Hansen M B, Nielsen S E, Berg K, "Re-Examination and Further Development of a Precise and Rapid Dye Method for Measuring Cell Growth/Cell Kill," *J Immunol. Methods,* 119:203–210, 1989.

Andersson B S, Sadeghi T, Siciliano M, Legerski R, Murray D, "Nucleotide Excision Repair Genes as Determinants of Cellular Sensitivity to Cyclophosphamide Analogs," *Cancer Chemother and Pharmacol,* In Press, 1995.

Andersson B S, Mroue M, Britten R A, Murray D, "The Role of DNA Damage in the Resistance of Human Chronic Myeloid Leukemia Cells to Cyclophosphamide Analogs," *Cancer Research,* 54:5394–5400, 1994.

What is claimed is:

1. A pharmaceutical composition for parenteral administration comprising a taxane analog and a solvent vehicle consisting essentially of dimethylacetamide (DMA), polyethylene glycol (PEG) and an aqueous lipid emulsion.

2. The pharmaceutical composition of claim 1, wherein said taxane analog is paclitaxel.

3. The pharmaceutical composition of claim 1, where the taxane analog is at concentrations of about 1 to about 5 mg/nl.

4. The pharmaceutical composition of claim 1, wherein said aqueous lipid emulsion is a soybean oil emulsion.

5. The pharmaceutical composition of claim 1, wherein said PEG has a molecular weight of about 400.

6. Amended) The pharmaceutical composition of claim 1, wherein the ratio of DMA to PEG is about 1:3 (v/v).

7. A method of preparing a paclitaxel composition for intravascular administration comprising the steps of:

dissolving paclitaxel in DMA at a concentration of up to about 100 mg/ml;

adding polyethylene glycol (PEG) to the paclitaxel solution at a ratio of DMA:PEG of about 1:3 (v/v) to achieve a paclitaxel stock formulation with a concentration of up to about 25 mg/ml paclitaxel; and adding an aqueous lipid emulsion to achieve a paclitaxel concentration of from about 1 to about 5 mg/ml. to produce a composition comprising paclitaxel and a solvent vehicle consisting essentially of dimethylacetamide (DMA), polyethylene glycol (PEG) and an aqueous lipid emulsion.

8. A pharmaceutical composition prepared by the method of claim 7.

9. A method of treating a paclitaxel sensitive tumor comprising: obtaining a pharmaceutical composition comprising paclitaxel dissolved in a solvent consisting essentially of dimethylacetamide (DMA) and polyethylene glycol (PEG) at a ratio of DMA:PEG of about 1:3 (v/v) and an aqueous lipid emulsion to achieve a final paclitaxel concentration of about 1 to 5 mg/ml; and contacting said tumor with said pharmaceutical composition.

10. The method of claim 9, wherein said tumor is in a subject and said pharmaceutical composition is administered parenterally.

11. The method of claim 10 wherein said subject is a human ovarian cancer, breast cancer, malignant lymphoma, lung cancer or Kaposi's sarcoma patient.

12. The method of claim 9 wherein said pharmaceutical composition is administered at a dosage of about 135 to about 250 mg/m$^2$ of body surface.

13. A paclitaxel stock formulation comprising about 25 mg/ml paclitaxel and a solvent vehicle consisting essentially of dimethylacetamide:polyethylene glycol in a v/v ratio of about 1:3.

14. The paclitaxel stock formulation of claim 13, wherein said polyethylene glycol has a molecular weight of about 400.

* * * * *

UNITED STATES PATENT AND TRADEMARK OFFICE
CERTIFICATE OF CORRECTION

PATENT NO. : 6,107,333
DATED : August 22, 2000
INVENTOR(S) : Borje S. Andersson

It is certified that error appears in the above-identified patent and that said Letters Patent is hereby corrected as shown below:

<u>Title page,</u>
Add -- Assignee: Board of Regents, The University of Texas System, Austin, Tex. --

<u>Column 17, claim 3,</u>
Line 7, delete "mg/nl" and substitute therefor -- mg/ml --.

<u>Column 17, claim 6,</u>
Line 12, delete "(Amended)".

Signed and Sealed this

Thirtieth Day of October, 2001

Attest:

NICHOLAS P. GODICI
Attesting Officer   Acting Director of the United States Patent and Trademark Office